(12) United States Patent
McLean (10) Patent No.: US 9,498,347 B2
(45) Date of Patent: Nov. 22, 2016

(54) EXPANDABLE INTERBODY FUSION DEVICE WITH NESTED CORRECTION SURFACE

(71) Applicant: SPINE WAVE, INC., Shelton, CT (US)

(72) Inventor: Scott McLean, Sandy Hook, CT (US)

(73) Assignee: SPINE WAVE, INC., Shelton, CT (US)

( * ) Notice: Subject to any disclaimer, the term of this patent is extended or adjusted under 35 U.S.C. 154(b) by 0 days.

(21) Appl. No.: 14/741,588

(22) Filed: Jun. 17, 2015

(65) Prior Publication Data

US 2015/0374509 A1    Dec. 31, 2015

Related U.S. Application Data

(60) Provisional application No. 62/016,903, filed on Jun. 25, 2014.

(51) Int. Cl.
*A61F 2/44* (2006.01)
*A61F 2/30* (2006.01)

(52) U.S. Cl.
CPC ............. *A61F 2/4455* (2013.01); *A61F 2/447* (2013.01); *A61F 2002/30538* (2013.01); *A61F 2002/30556* (2013.01); *A61F 2002/30599* (2013.01)

(58) Field of Classification Search
CPC .......................................... A61F 2/4455–2/447
See application file for complete search history.

(56) References Cited

U.S. PATENT DOCUMENTS

| 6,176,882 | B1 * | 1/2001 | Biedermann | ........... | A61F 2/447 |
| | | | | | 623/17.11 |
| 6,193,757 | B1 | 2/2001 | Foley et al. | | |
| 6,436,140 | B1 | 8/2002 | Liu et al. | | |
| 6,595,998 | B2 | 7/2003 | Johnson et al. | | |
| 6,830,589 | B2 | 12/2004 | Erickson | | |
| 7,618,459 | B2 | 11/2009 | Justin et al. | | |
| 7,931,688 | B2 | 4/2011 | Landry et al. | | |
| 7,967,867 | B2 | 6/2011 | Barreiro et al. | | |
| 8,480,748 | B2 | 7/2013 | Poulos | | |
| 8,628,576 | B2 | 1/2014 | Triplett et al. | | |
| 8,685,098 | B2 | 4/2014 | Glerum et al. | | |
| 8,715,351 | B1 | 5/2014 | Pinto | | |
| 8,900,312 | B2 | 12/2014 | McLean et al. | | |
| 9,084,686 | B1 * | 7/2015 | McLean | ................ | A61F 2/4455 |
| 2004/0162618 | A1 | 8/2004 | Mujwid et al. | | |
| 2008/0147193 | A1 * | 6/2008 | Matthis | ................. | A61F 2/4425 |
| | | | | | 623/17.16 |
| 2010/0286779 | A1 | 11/2010 | Thibodeau | | |
| 2013/0211525 | A1 * | 8/2013 | McLuen | ............... | A61F 2/4455 |
| | | | | | 623/17.16 |
| 2013/0274883 | A1 * | 10/2013 | McLuen | ................ | A61F 2/447 |
| | | | | | 623/17.16 |
| 2014/0100662 | A1 | 4/2014 | Patterson et al. | | |
| 2014/0148903 | A1 | 5/2014 | Pinto | | |

(Continued)

OTHER PUBLICATIONS

PCT Search Report and Written Opinion for PCT/US2015/036132, dated Sep. 16, 2015.

*Primary Examiner* — David Bates
*Assistant Examiner* — Olivia C Chang
(74) *Attorney, Agent, or Firm* — Hoffmann & Baron, LLP (57) ABSTRACT

An expandable interbody fusion device includes a superior endplate and an inferior endplate. The superior endplate is designed and structured to be angled; the angled surface of the superior endplate becomes prominent upon expansion. The inferior endplate has a bounded cavity in which the superior endplate is fully nested in an unexpanded condition. In a fully expanded condition, the entire outer surface of the superior endplate moves out of the cavity and above an upper surface of the inferior endplate.

19 Claims, 9 Drawing Sheets

(56) References Cited

U.S. PATENT DOCUMENTS

2014/0236296 A1* 8/2014 Wagner .................. A61F 2/447 623/17.15

2015/0012097 A1* 1/2015 Ibarra ..................... A61F 2/447 623/17.15

2015/0190242 A1* 7/2015 Blain ................. A61F 2/30771 623/17.12

* cited by examiner

EXPANDABLE INTERBODY FUSION DEVICE WITH NESTED CORRECTION SURFACE

CROSS-REFERENCE TO RELATED APPLICATION

This application claims the benefit of U.S. Provisional Patent Application No. 62/016,903 filed Jun. 25, 2014, the entire contents of which are incorporated by reference herein.

FIELD OF THE INVENTION

The subject invention relates to the field of spinal implants, and more particularly, to expandable interbody fusion devices with nested correction surface.

BACKGROUND OF THE INVENTION

Spinal implants such as interbody fusion devices are used to treat degenerative disc disease and other damages or defects in the spinal disc between adjacent vertebrae. The disc may be herniated or suffering from a variety of degenerative conditions, such that the anatomical function of the spinal disc is disrupted. Most prevalent surgical treatment for these conditions is to fuse the two vertebrae surrounding the affected disc. In most cases, the entire disc will be removed, except for a portion of the annulus, by way of a discectomy procedure. A spinal fusion device is then introduced into the intradiscal space and suitable bone graft or bone substitute material is placed substantially in and/or adjacent the device in order to promote fusion between two adjacent vertebrae.

Certain spinal devices for achieving fusion are also expandable so as to correct disc height between the adjacent vertebrae. Examples of expandable interbody fusion devices are described in U.S. Pat. No. 6,595,998 entitled "Tissue Distraction Device", which issued on Jul. 22, 2003 (the '998 patent), U.S. Pat. No. 7,931,688 entitled "Expandable Interbody Fusion Device", which issued on Apr. 26, 2011 (the '688 patent), U.S. Pat. No. 7,967,867 entitled "Expandable Interbody Fusion Device", which issued on Jun. 28, 2011 (the '867 patent), U.S. Pat. No. 8,900,312, entitled "Expandable Interbody Fusion Device with Graft Chambers", which issued on Dec. 2, 2014 ("the '312 patent"), and Non-Provisional patent application Ser. No. 14/474,555 entitled "Expandable Spinal Interbody Fusion Device", which filed on Sep. 2, 2014 ("the '555 application"), all of which are owned by the assignee herein and the contents of which are hereby incorporated by reference in their respective entireties.

An issue that has arisen regarding such interbody fusion devices is, during a spinal fusion procedure, the difficulty in inducing changes in the angle between vertebral endplates to restore normal anatomic alignment, in particular for lordosis. While this can be achieved by altering angles of the endplates of the device, altering angle naturally increases initial implant profile. Accordingly, there is a need to develop an improved expandable interbody fusion device with a design such that the device remains in a minimum profile while being capable of inducing changes in the angle between vertebral endplates.

SUMMARY OF THE INVENTION

An expandable interbody fusion device is provided herein with an angled superior endplate structure such that upon expansion, the angled surface of the superior endplate becomes prominent and contacts the vertebral endplate to influence the vertebral body in a desired manner. Advantageously, an expandable interbody fusion device may be provided with a design so as to provide a minimum non-expanded profile while inducing changes in the angle between vertebral endplates.

DESCRIPTION OF THE FIGURES

FIG. 9a is a cross-sectional view of the expandable interbody fusion device of FIG. 8a as seen along viewing line 9a-9a of FIG. 8a.

DESCRIPTION OF THE EMBODIMENTS

For the purposes of promoting and understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 1:
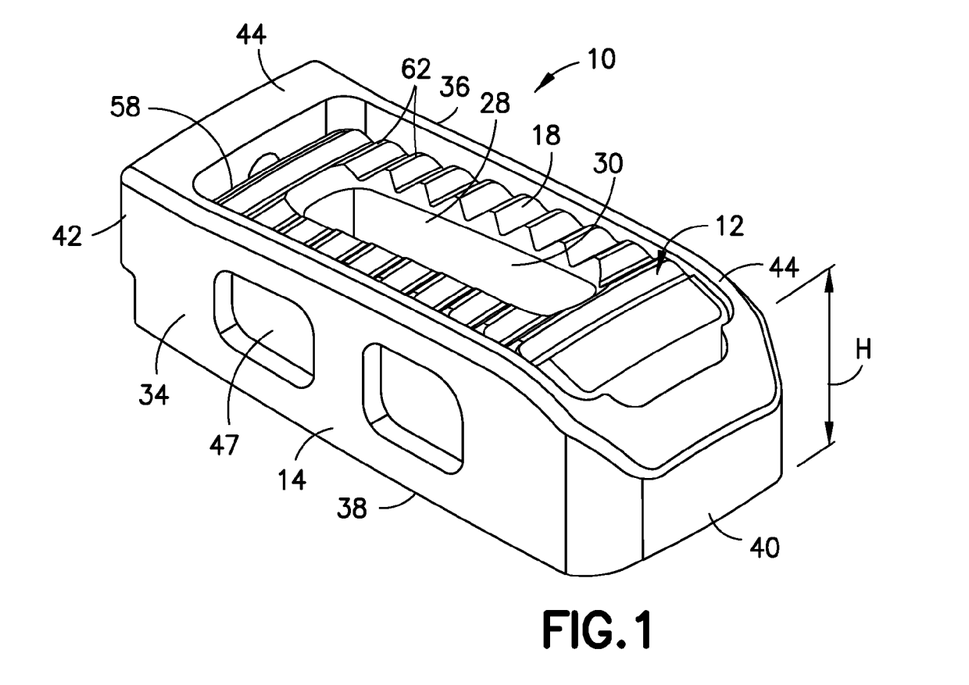
FIG. 1 is a top perspective view of an expandable interbody fusion device in an unexpanded condition, used for a posterior approach, in accordance with one embodiment of the present invention.

Referring to FIGS. 1-9c, an expandable interbody fusion device 10 used for a posterior approach, a procedure in which the device 10 is accessed from the back of the spine, is shown. The expandable interbody fusion device 10 includes a superior endplate 12 and an inferior endplate 14. The expandable interbody fusion device 10 has a height H between the superior and inferior endplates 12, 14 in an unexpanded condition as illustrated in FIG. 1 that is less than the normal anatomic height of a typical intradiscal space between opposing vertebral bodies. In this manner, the expandable interbody fusion device 10 may be placed into an intradiscal space and expanded, as described below, to cause distraction of the adjacent vertebral bodies.

Figure 2:
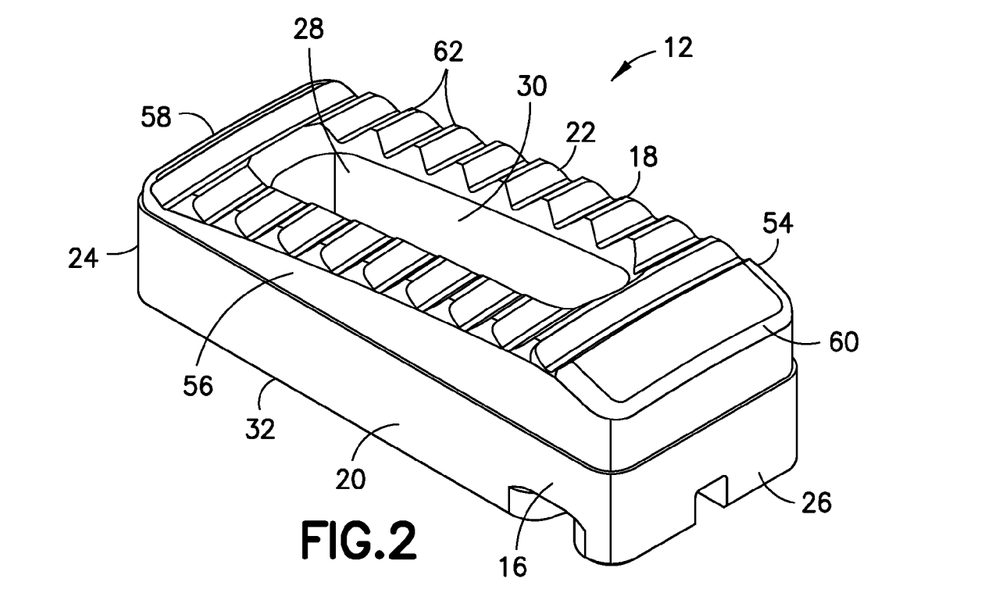
FIG. 2 is a top perspective view of a superior endplate of the expandable interbody fusion device of FIG. 1.

The superior endplate 12 is elongated and comprises a hub 16 and an outer surface 18. The hub includes a pair of side surfaces 20, 22 extending longitudinally on each side of the hub 16. The hub 16 also includes a pair of end surfaces 24, 26 extending respectively at the proximal rear end and the distal front end of the superior endplate 12. The hub 16 is dimensioned and configured to be closely accommodated within the inferior endplate 14 for movement in a direction relative to the inferior endplate 14 toward an adjacent vertebral body.

The superior endplate 12 includes a graft chamber 28 defined by an opening 30 extending through the outer surface 18 and a lower surface 32 of the hub 16. Opening 30 may be longitudinally centered or situated to lie more adjacent to the proximal or rear end of the device 10. In accordance with one arrangement, the superior endplate 12 is formed of a biocompatible polymer such as polyethyletheylketone (PEEK). PEEK is used in fusion applications for its combination of strength, biocompatibility, and elasticity which is similar to human bone. Other composites may include derivatives of PEEK such as carbon fiber reinforced PEEK and PEKK, respectively. Alternatively, the superior endplate 12 may be made of one or more materials having suitable properties for a spinal fusion procedure and the promotion of bone growth, including strength, weight, rigidity, etc. In a particular aspect, the superior endplate 12 may further include an upper endcap that defines the outer surface 18. The endcap may be a separate plate formed of material for the promotion of bone growth, such as titanium, and may be attached to the endplate 12 with suitable conventional techniques. As an alternative, the outer surface 18 may be defined by a coating of a suitable layer of bone growth promotion material, such as titanium, which may be deposited by conventional techniques.

Figure 3:
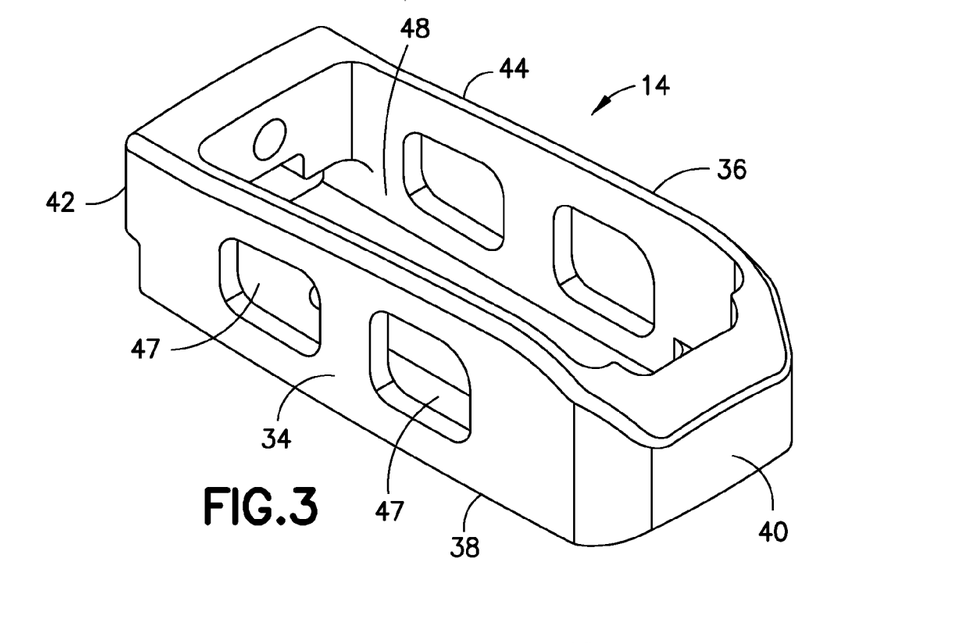
FIG. 3 is a top perspective view of an inferior endplate of the expandable interbody fusion device of FIG. 1.
Figure 4:
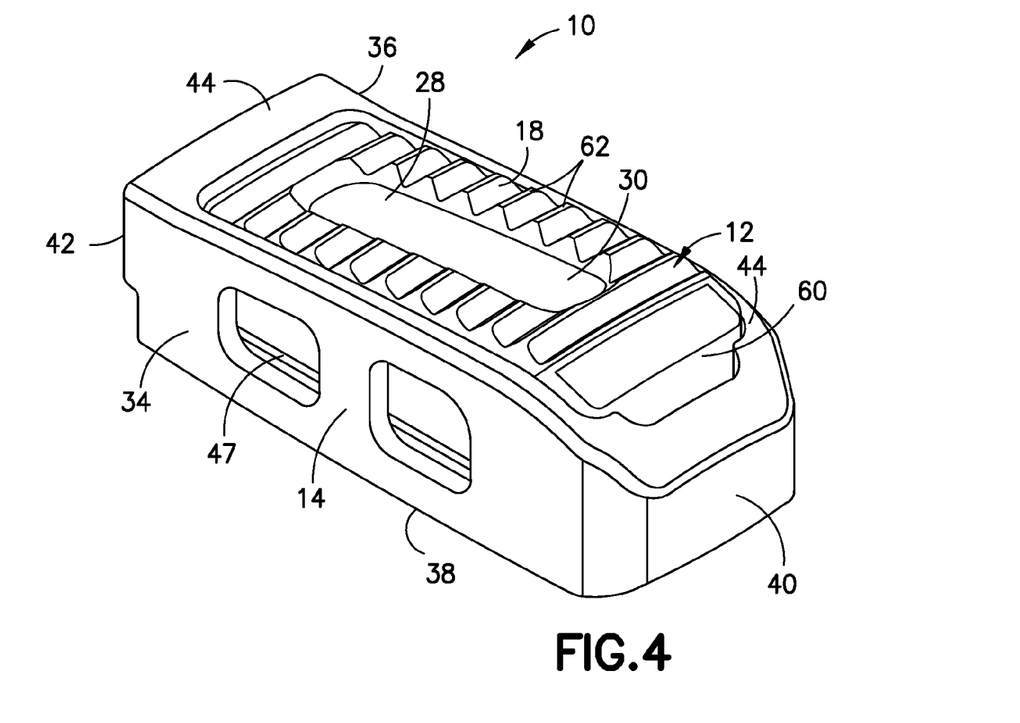
FIG. 4 is a top perspective view of the partially expanded interbody fusion device of FIG. 1.
Figure 5:
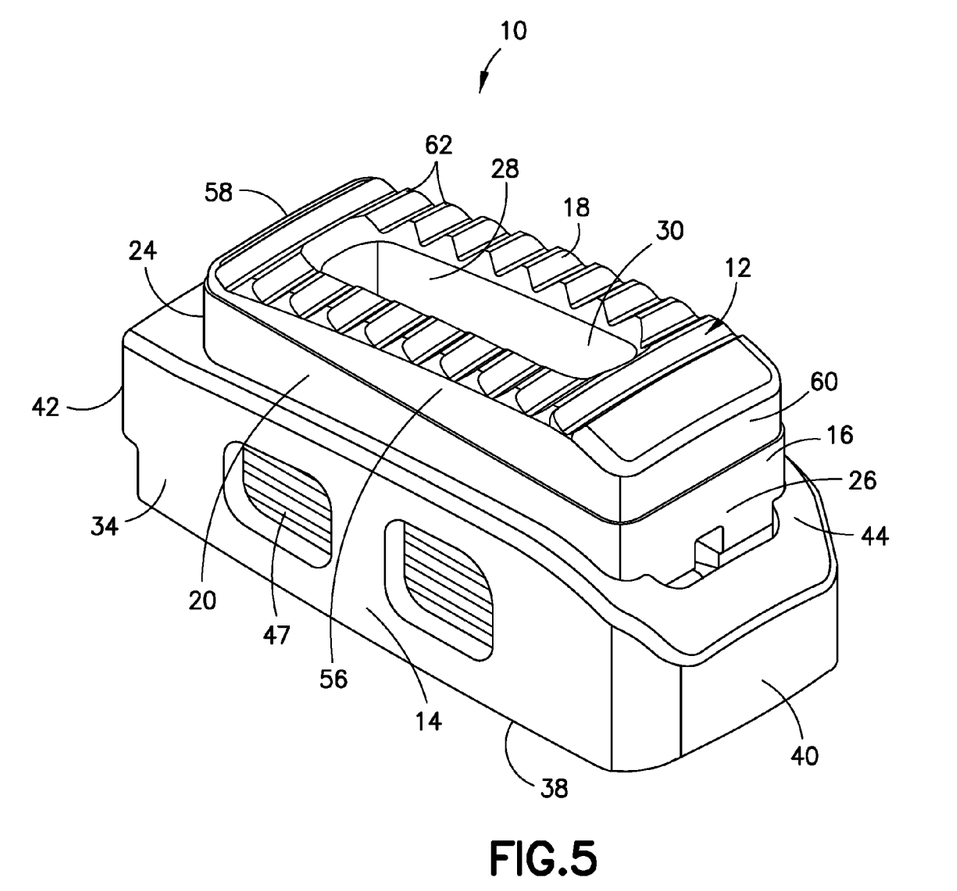
FIG. 5 is a top perspective view of the fully expanded interbody fusion device of FIG. 1.

Referring to FIGS. 1 and 3-9c, the inferior endplate 14 is elongated and comprises a pair of oppositely spaced apart lateral sidewalls 34, 36 extending along the longitudinal direction and projecting upwardly from a lower outer surface 38 of the inferior endplate 14. A pair of oppositely spaced apart endwalls 40, 42, defining an anterior endwall 40 and a posterior endwall 42, extends laterally across the device 10 and projects upwardly from the lower outer surface 38. Each of the endwalls 40, 42 includes an upper surface that jointly with an upper surface of sidewalls 34, 36 defines an upper surface 44 of the inferior endplate 14. Referring more particularly to FIG. 3, the sidewalls 34, 36 together with the endwalls 40, 42 form an open, upwardly facing fully bounded interior cavity 48. The interior cavity 48 is dimensioned and configured to closely accommodate the superior endplate 12 in between the sidewalls 34, 36 and the endwalls 40, 42 of the inferior endplate 14 in an unexpanded condition.

Figure 9A:
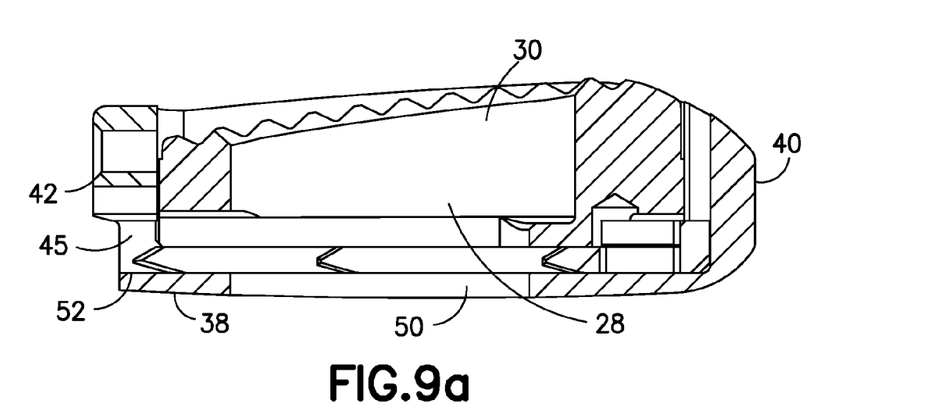
Figure 9B:
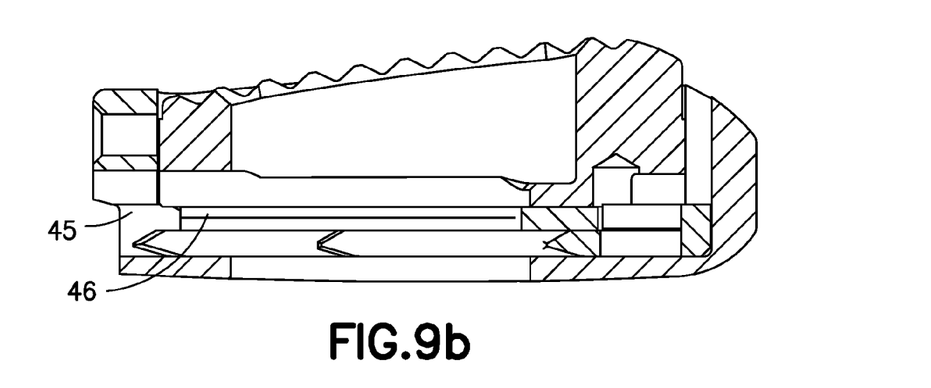
FIG. 9b is a cross-sectional view of the expandable interbody fusion device of FIG. 8b as seen along viewing line 9b-9b of FIG. 8b.
Figure 9C:
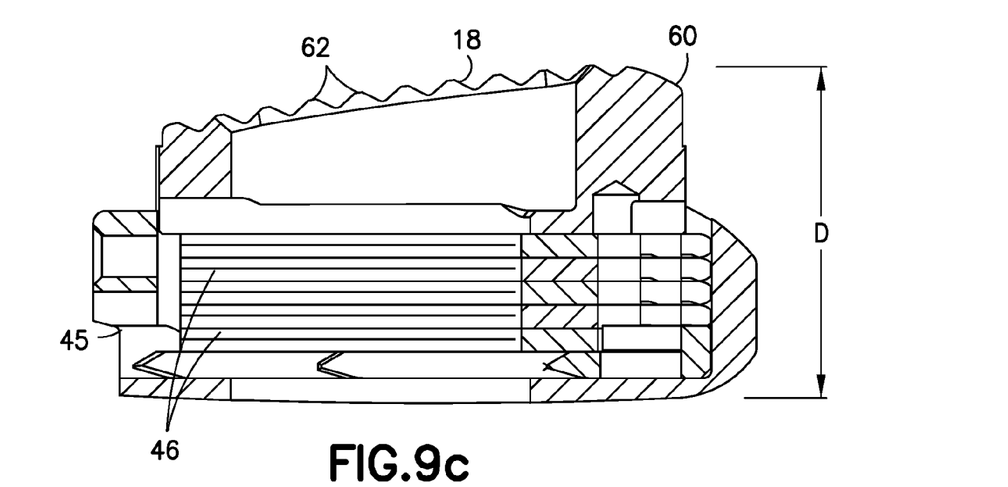
FIG. 9c is a cross-sectional view of the expandable interbody fusion device of FIG. 8c as seen along viewing line 9c-9c of FIG. 8c.

The inferior plate 14 as shown in FIGS. 9a-c defines an insert opening 45 through the posterior endwall 42 of the expandable interbody fusion device 10 through which a series of insertion structures in the form of flat, substantially planar inserts 46, may be introduced one below the other. A plurality of windows 47 may be formed through the sidewalls 34, 36 as shown in FIGS. 1, 3 and 4-6c so as to allow visual observation of the expansion of the device 10 and insertion of the series of inserts 46, which will be described in detail below, by suitable imaging techniques, such as fluoroscopy.

Still referring to FIGS. 9a-c, the inferior endplate 14 includes a graft chamber defined by an opening 50 extending through the lower outer surface 38 and an upper support surface 52 in communication with the interior cavity 48. Opening 50 is situated to lie at least in partial alignment with the opening 30 in the superior endplate 12. In accordance with one arrangement, the inferior endplate 12 is formed of a material different from the material of the superior endplate 12. In this aspect, the inferior endplate 12 may be formed of a biocompatible metal, such as titanium, for its strength properties. Titanium is chosen for strength, biocompatibility, processing capability, and fluoroscopic imaging properties (radiolucency). Other alternative materials include cobalt chrome, stainless steel (both stronger than titanium but much less radiolucent), or biocompatible ceramics such as silicon nitride or zirconia, which are radiolucent. Titanium and silicon nitride have demonstrated good apposition to bone and superior to PEEK. In this regard where inferior endplate 14 is formed of titanium, the lower outer surface 38 would provide for the promotion of bone growth. Where the inferior endplate 14 is not formed of a bone growth promotion material, the lower outer surface 38 may be coated with a suitable layer of bone growth promotion material, such as titanium, and deposited in a conventional manner as described hereinabove. Alternatively, the inferior endplate 14 could be made of one or more materials having suitable properties for a spinal fusion procedure and the promotion of bone growth, including strength, weight, rigidity, etc. Generally, the outer surface of the inferior endplate 14 is convex between the lateral sidewalls 34, 36.

In one approach, the present invention contemplates that inserts 46 may be introduced into the expandable interbody fusion device 10 through insert opening 45 after the superior and inferior endplates 12, 14 are separated as illustrated in FIGS. 6a-c, 7a-c and 9a-c and the device 10 is expanded incrementally, as more fully described in the '555 application, incorporated herein by reference. The height of the device 10 is increased during expansion within the intradiscal space to thereby ultimately restore the normal anatomic height of the disc space. Each of inserts 46 may define an opening (not shown) extending therethrough, which is configured to receive a material for promotion of bone growth.

An alternative expansion approach that separates the superior and inferior endplates 12, 14 is described in the present assignee's '998 patent, '688 patent and '867 patent, each of which is incorporated by reference herein. These Patents each disclose introducing insertion structures, which may be in the form of expansion wafers, in a percutaneous approach to incrementally expand the interbody fusion device upon insertion of such wafers and thereby distract opposing vertebral bodies to stabilize the spine and correct spinal height In the depicted embodiment, as illustrated in FIGS. 2, 5, 6c and 7c, the outer surface 18 of the superior endplate 12 is formed and bounded by oppositely spaced lateral edges 54, 56 and oppositely spaced posterior edge 58 and anterior edge 60. The outer surface 18 closer to the anterior edge 60 is configured to be more prominent than the posterior edge 58. In this manner, the outer surface 18 of the superior endplate 12 defines an anatomic correction surface generally inclining downwardly in an anterior-posterior direction toward the posterior edge 58. The anterior edge 60 may be located higher than the posterior edge 58. A plurality of ridges 62 may be integrally formed on the outer surface 18, with each of the ridges 62 protruding upwardly. The ridges 62 may provide for enhanced engagement with an adjacent vertebral body. It is noted that one or more of the ridges 62 may be more prominent than the anterior edge 60. In this manner, one or more of the ridges 62 may define an apex of the outer surface 18. Generally, the outer surface 18 of the superior endplate 14 may be provided with an overall convex shape between the posterior and anterior edges 58, 60. In the depicted embodiment, the outer surface 18 is attached to the hub 16; alternately, the outer surface 28 may be formed integrally therewith.

As seen from FIGS. 1, 6a, 7a and 9a, in the unexpanded condition, the superior endplate 12 lies fully nested within the bounds of the interior cavity 48 of the inferior endplate 14. The anterior edge 60 of the outer surface 18 of the superior endplate 12 may be located to be substantially flush with, or recessed below, the upper surface 44 of the inferior endplate 14 in the fully nested state of the superior endplate 12. The posterior edge 58 of the outer surface 18 of the superior endplate 12 is recessed within the interior cavity 48 below the upper surface 44 of the inferior endplate 14 with the superior endplate 12 being fully nested.

Figure 6A:
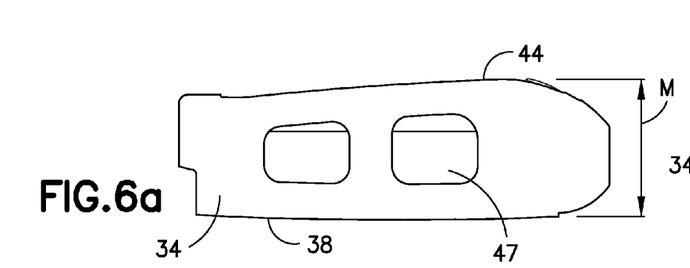
FIG. 6a is a side view of the unexpanded interbody fusion device of FIG. 1.
Figure 6B:
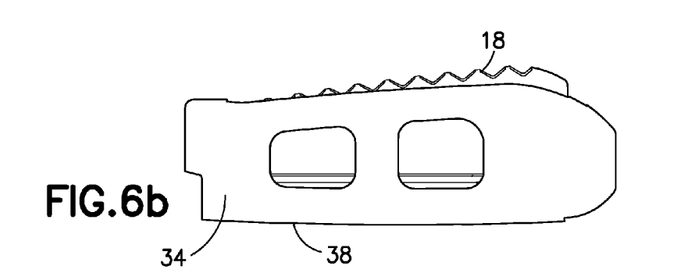
FIG. 6b is a side view of the partially expanded interbody fusion device of FIG. 4.
Figure 6C:
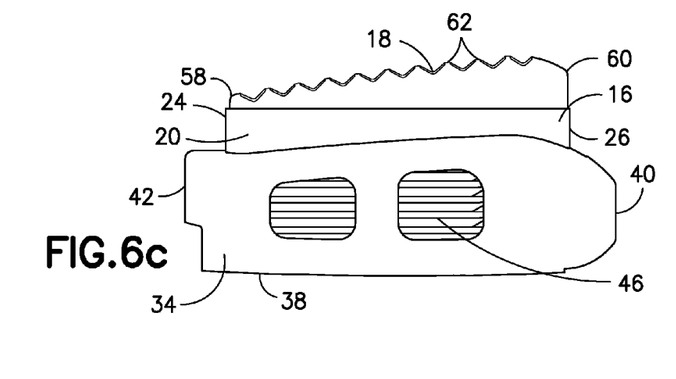
FIG. 6c is a side view of the fully expanded interbody fusion device of FIG. 5.
Figure 7A:
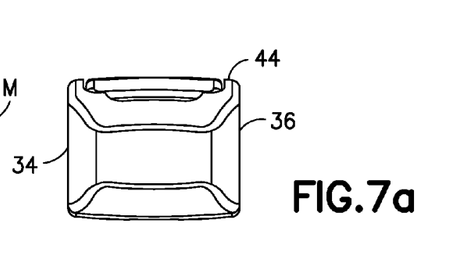
FIG. 7a is a front view of the unexpanded interbody fusion device of FIG. 1.
Figure 7B:
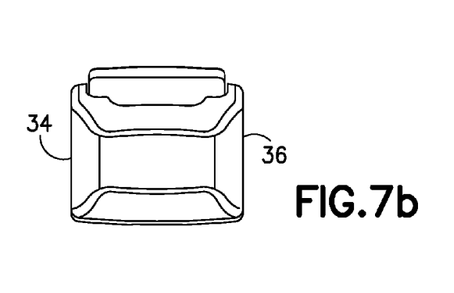
FIG. 7b is a front view of the partially expanded interbody fusion device of FIG. 4.
Figure 7C:
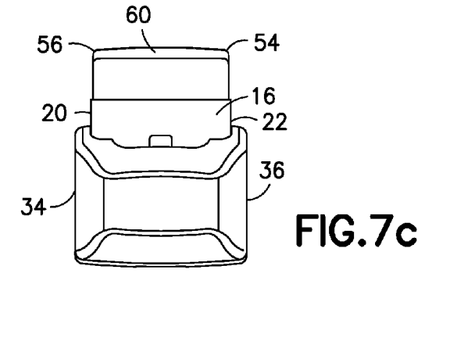
FIG. 7c is a front view of the fully expanded interbody fusion device of FIG. 5.
Figure 8A:
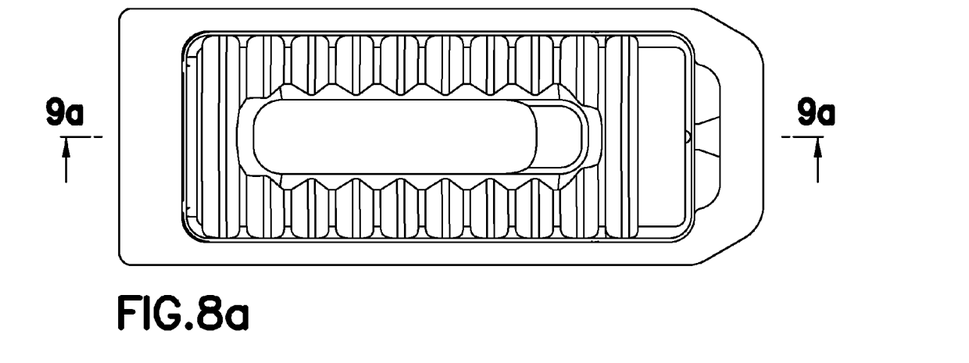
FIG. 8a is a top view of the unexpanded interbody fusion device of FIG. 1.
Figure 8B:
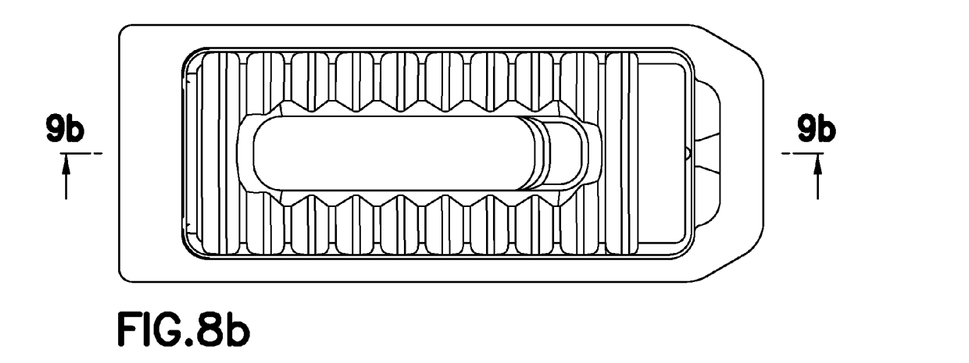
FIG. 8b is a top view of the partially expanded interbody fusion device of FIG. 4.
Figure 8C:
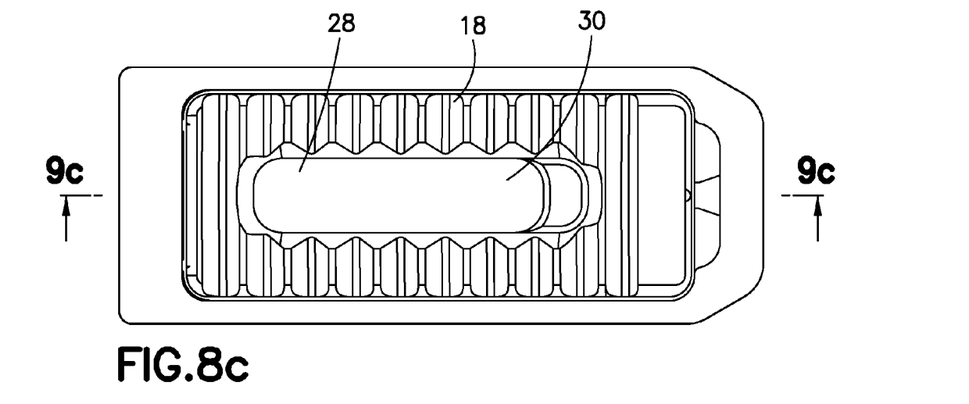
FIG. 8c is a top view of the fully expanded interbody fusion device of FIG. 5.

Overall, the expandable interbody fusion device 10 in an unexpanded state may be provided with a lordotic shape, whereby the distal front portion of the device 10 has a height greater than the proximal rear portion of the device 10. Furthermore, since the device 10 is lordotic, the unexpanded height of the inferior endplate 14 is defined by the maximum distance M between the lower outer surface 38 and the upper surface 44 of the inferior endplate 14 as illustrated in FIG. 6a.

When the expandable interbody fusion device 10 is inserted into a intradiscal space during a spinal procedure and the expandable interbody fusion device 10 is expanded, the outer surface 18 of the superior endplate 12 is caused to become proud of the inferior endplate 14 and contact one of two opposing vertebral bodies with the inferior endplate 14 contacting the other vertebral body. Continued expansion of the expandable interbody fusion device 10 causes the inclination of the outer surface 18 to act against the vertebral endplate. The angular disposition may provide a corrective effect to the alignment of the vertebra. When a sufficiently expanded condition is reached as illustrated in FIGS. 5, 6c, 7c and 9c, both the posterior and anterior edges 58, 60 of the outer surface 18 of the superior endplate 12 move completely out of the interior cavity 48 of the inferior endplate 14 and above the upper surface 44 of the inferior endplate 14. The fully expanded height of the expandable interbody fusion device 10 is defined by the distance D between the lower outer surface 38 of the inferior endplate 14 and the ridge 62 of the superior endplate 12 at the highest point as seen in FIG. 9c.

Figure 10:
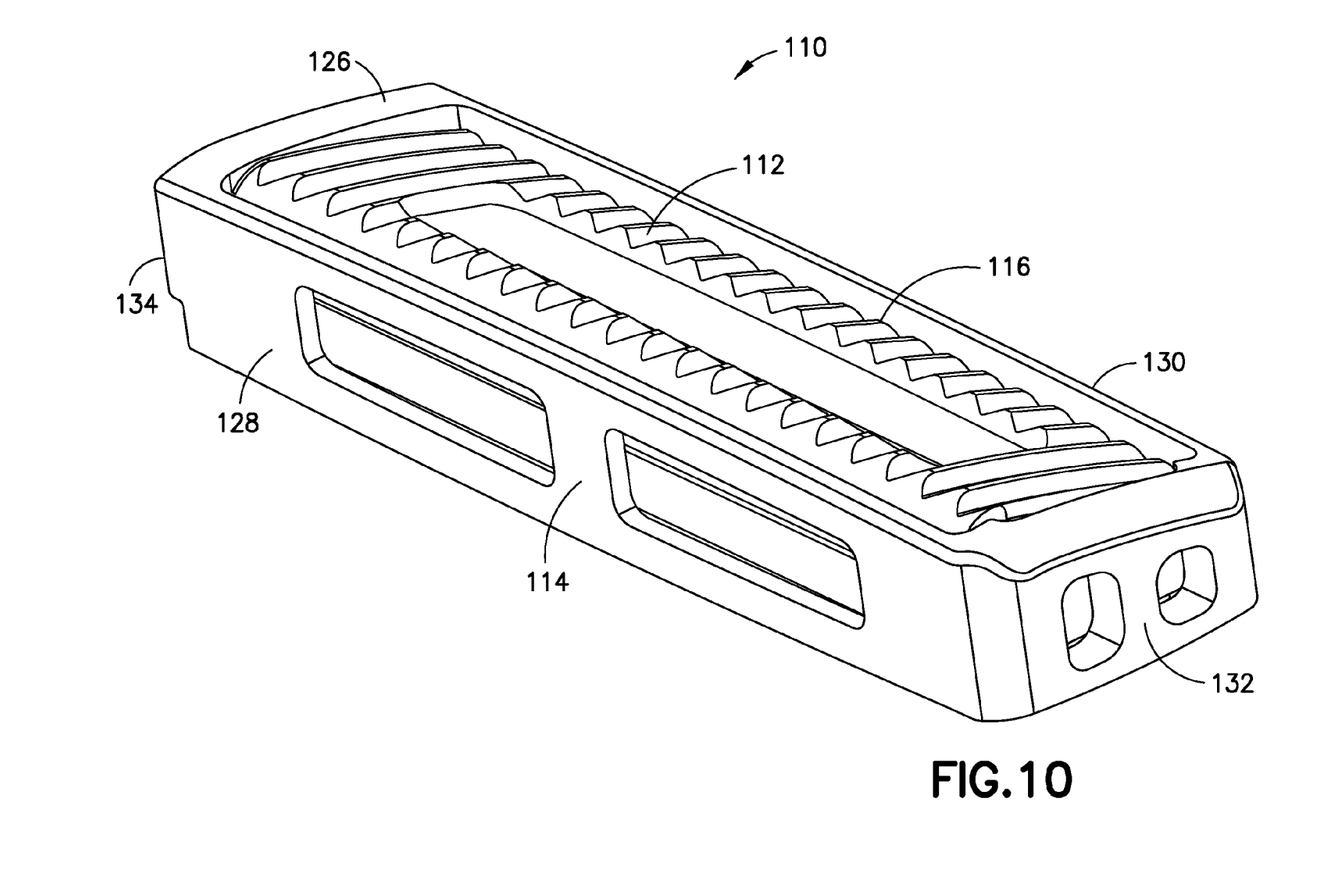
FIG. 10 is a top perspective view of an expandable interbody fusion device in the unexpanded condition, used for a lateral approach, in accordance with alternate embodiment of the present invention.
Figure 11:
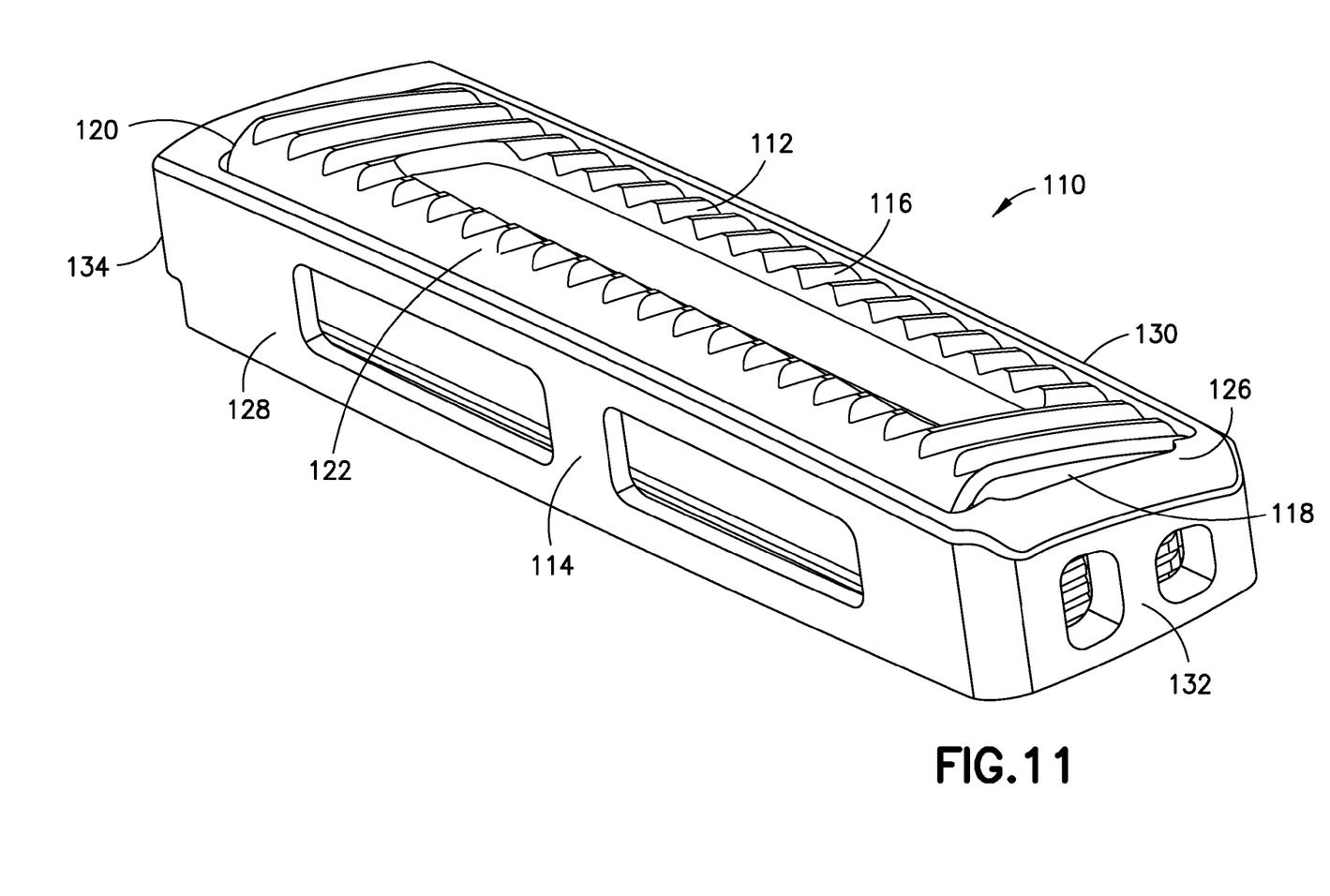
FIG. 11 is a top perspective view of the partially expanded interbody fusion device of FIG. 10.
Figure 12:
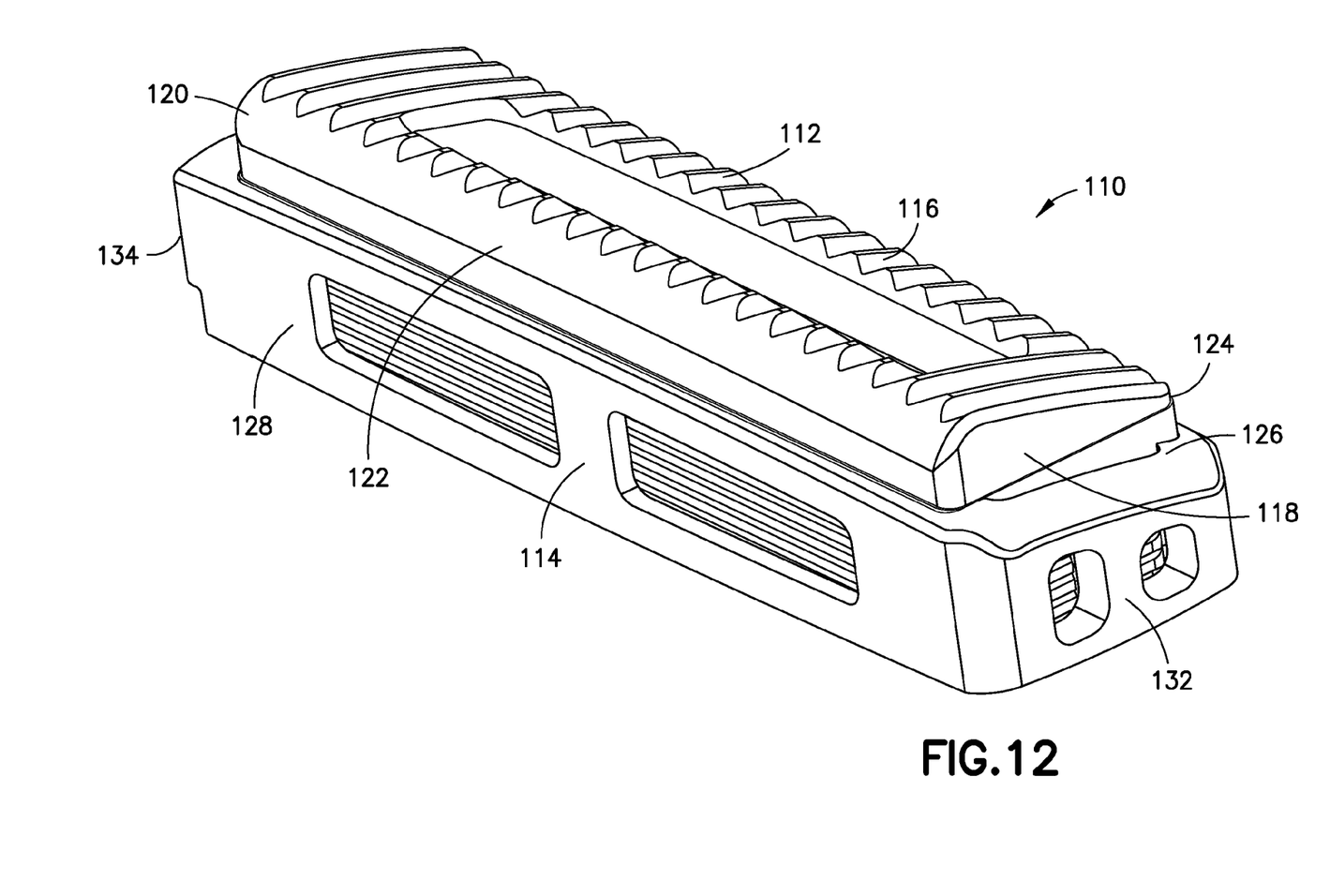
FIG. 12 is a top perspective view of the fully expanded interbody fusion device of FIG. 10.

In an alternate embodiment, referring to FIGS. 10-12, an expandable interbody fusion device 110 used for a lateral approach, a procedure in which the device is introduced into the intradiscal space from the side of the spine, is shown. The expandable interbody fusion device 110 is elongate and includes a superior endplate 112 and an inferior endplate 114. The expandable interbody fusion device 110 for the lateral approach is structurally similar to the device 10 for a posterior approach.

The superior endplate 112 includes an outer surface 116 which is formed and bounded by oppositely spaced distal and proximal edges 118, 120 and a pair of oppositely spaced, longitudinally extending lateral edges, defining a higher lateral edge 122 and a lower lateral edge 124, extending longitudinally therebetween. The outer surface 116 defines an anatomic correction surface generally inclining downwardly in a lateral direction of device 110 toward the lower lateral edge 124. Lower lateral edge 124 is intended during insertion of device 110 to lie adjacent the posterior portion of the disc space with higher lateral edge 122 being adjacent to the anterior portion of the disc space. Generally, the outer surface 116 of the superior endplate 112 may be convex between the higher and lower lateral edges 122, 124 and may be convex between the distal and proximal edges 118, 120. In addition, the outer surface of the inferior endplate 114 may be generally convex between lateral sidewalls 128, 130 and may be convex between distal and proximal sidewalls 132, 134.

In the unexpanded condition shown in FIG. 10, the superior endplate 112 is received within the interior cavity of inferior endplate 114 such that the outer surface 116 lies fully nested within the bounds of the interior cavity of inferior endplate 114. In this condition, at least posterior edge 124 of superior endplate 112 is recessed below the upper surface 126 of inferior endplate 114. Anterior edge 122 may also be recessed below or substantially flush with outer surface 126. Superior endplate 112 is movable in a direction of expansion relative to inferior endplate 114 in a manner as shown in FIG. 11 and as explained hereinabove such that upon expansion at least anterior edge 122 projects outwardly above upper surface 126 of inferior endplate 114. In the expanded condition as shown in FIG. 12 posterior edge 124 projects outwardly above upper surface 126 of inferior endplate 114 and anterior edge 122 is higher than posterior edge 124.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. An expandable interbody fusion device for implantation into an intradiscal space between two opposing vertebral bodies of a spine, comprising:
   a superior endplate having an outer surface configured to contact one of said vertebral bodies, said outer surface including at least two generally opposite spaced edges, said outer surface defining an anatomic correction surface being inclined downwardly away from a location proximate one of said edges defining a higher edge toward a location proximate the other of said edges defining a lower edge; and
   an inferior endplate having opposing spaced apart sidewalls and opposing spaced apart distal and proximal endwalls defining therewithin an open interior cavity, said sidewalls, said distal and proximal endwalls each having an upper surface that jointly define an upper surface of said inferior endplate, said superior endplate being received within said interior cavity such that in an unexpanded condition said outer surface of said superior endplate defining said anatomic correction surface lies fully nested within the bounds of said cavity with at least said lower edge being entirely recessed within said cavity below the upper surface of said inferior endplate, said superior endplate being movable in a direction of expansion relative to said inferior endplate toward said one vertebral body such that upon expansion at least the higher edge of said outer surface of said superior endplate projects outwardly above the upper surface of said inferior endplate.

2. The expandable interbody fusion device of claim 1, wherein said inferior endplate has a lower outer surface to contact the other vertebral body, an unexpanded height of said inferior endplate being defined by the maximum distance between the lower outer surface of said inferior endplate and the upper surface of said inferior endplate.

3. The expandable interbody fusion device of claim 2, wherein in the unexpanded condition said higher edge of said outer surface of said superior endplate is substantially flush with the upper surface of said inferior endplate.

4. An expandable interbody fusion device for implantation into an intradiscal space between two opposing vertebral bodies of a spine, comprising:
  a superior endplate having an outer surface configured to contact one of said vertebral bodies, said outer surface including at least two generally opposite spaced edges, said outer surface defining an anatomic correction surface being inclined downwardly away from one of said edges defining a higher edge toward the other of said edges defining a lower edge;
  an inferior endplate having opposing spaced apart sidewalls and opposing spaced apart distal and proximal endwalls defining therewithin an open interior cavity, said sidewalls, said distal and proximal endwalls each having an upper surface that jointly define an upper surface of said inferior endplate, said superior endplate being received within said interior cavity such that in an unexpanded condition said outer surface of said superior endplate defining said anatomic correction surface lies fully nested within the bounds of said cavity with at least said lower edge being recessed within said cavity below the upper surface of said inferior endplate, said superior endplate being movable in a direction of expansion relative to said inferior endplate toward said one vertebral body such that upon expansion at least the higher edge of said outer surface of said superior endplate projects outwardly above the upper surface of said inferior endplate; and
  an insertion structure between said superior endplate and said inferior endplate,
  wherein, said superior endplate, said inferior endplate and said insertion structure each have an opening therethrough, said openings being in communication and configured for receipt of a material for the promotion of bone growth.

5. The expandable interbody fusion device of claim 4, wherein said insertion structure includes at least one insert slidably received between said superior endplate and said inferior endplate.

6. The expandable interbody fusion device of claim 5, wherein in an expanded condition the lower edge of said outer surface of said superior endplate projects outwardly above the upper surface of said inferior endplate.

7. The expandable interbody fusion device of claim 6, wherein said insertion structure includes at least two inserts slidably received between said superior endplate and said inferior endplate, said at least two inserts being disposed one below the other in the direction of expansion.

8. An expandable interbody fusion device for implantation from a lateral aspect into an intradiscal space between two opposing vertebral bodies of a spine, comprising:
  an elongated superior endplate having an outer surface configured to contact one of said vertebral bodies, said outer surface being bounded by opposite, longitudinally spaced distal and proximal edges and a pair of generally longitudinally extending oppositely spaced apart lateral edges extending therebetween, said outer surface defining an anatomic correction surface being inclined downwardly away from one of said lateral edges defining a higher edge toward the other of said lateral edges defining a lower edge; and
  an elongated inferior endplate having a lower outer surface configured to contact the other vertebral body, said inferior endplate having generally longitudinally extending opposing spaced apart lateral sidewalls and opposing spaced apart distal and proximal endwalls defining therewithin an open interior cavity, said sidewalls, said distal and proximal endwalls each having an upper surface that jointly define an upper surface of said inferior endplate, an unexpanded height of said inferior endplate being defined by the maximum distance between the lower outer surface of said inferior endplate and the upper surface of said inferior endplate, said superior endplate being received within said interior cavity such that in an unexpanded condition said outer surface of said superior endplate defining said anatomic correction surface lies fully nested within the bounds of said cavity with at least said lower lateral edge being entirely recessed within said cavity below the upper surface of said inferior endplate, said superior endplate being movable in a direction of expansion relative to said inferior endplate toward said one vertebral body such that upon expansion at least said higher lateral edge of said outer surface of said superior endplate projects outwardly above the upper surface of said inferior endplate.

9. The expandable interbody fusion device of claim 8, wherein in the unexpanded condition said higher lateral edge of said outer surface of said superior endplate is substantially flush with the upper surface of said inferior endplate.

10. The expandable interbody fusion device of claim 9, wherein in an expanded condition the lower lateral edge of said outer surface of said superior endplate projects outwardly above the upper surface of said inferior endplate.

11. The expandable interbody fusion device of claim 10, wherein the outer surface of said superior endplate is generally convex between the higher lateral edge and the lower lateral edge.

12. The expandable interbody fusion device of claim 11, wherein the outer surface of said inferior endplate is generally convex between said lateral sidewalls.

13. The expandable interbody fusion device of claim 12, wherein the outer surface of said superior endplate is generally convex between the distal edge and the proximal edge.

14. The expandable interbody fusion device of claim 12, wherein the outer surface of said inferior endplate is generally convex between the distal sidewall and the proximal sidewall.

15. An expandable interbody fusion device for implantation from a posterior aspect into an intradiscal space between two opposing vertebral bodies of a spine, comprising:

an elongated superior endplate having an outer surface configured to contact one of said vertebral bodies, said outer surface being bounded by opposite, longitudinally spaced anterior and posterior edges and a pair of generally longitudinally extending oppositely spaced apart lateral edges extending therebetween, said outer surface defining an anatomic correction surface being inclined downwardly away from said anterior edge toward the posterior edge; and an elongated inferior endplate having a lower outer surface configured to contact the other vertebral body, said inferior endplate having generally longitudinally extending opposing spaced apart lateral sidewalls and opposing spaced apart anterior and posterior endwalls defining therewithin an open interior cavity, said sidewalls, said anterior and posterior endwalls each having an upper surface that jointly define an upper surface of said inferior endplate, an unexpanded height of said inferior endplate being defined by the maximum distance between the lower outer surface of said inferior endplate and the upper surface of said inferior endplate, said superior endplate being received within said interior cavity such that in an unexpanded condition said outer surface of said superior endplate defining said anatomic correction surface lies fully nested within the bounds of said cavity with at least said posterior edge being entirely recessed within said cavity below the upper surface of said inferior endplate, said superior endplate being movable in a direction of expansion relative to said inferior endplate toward said one vertebral body such that upon expansion at least the anterior edge of said outer surface of said superior endplate projects outwardly above the upper surface of said inferior endplate.

16. The expandable interbody fusion device of claim 15, wherein in an expanded condition the posterior edge of said outer surface of said superior endplate projects outwardly above the upper surface of said inferior endplate.

17. The expandable interbody fusion device of claim 16, wherein the outer surface of said superior endplate is generally convex between the anterior edge and the posterior edge.

18. The expandable interbody fusion device of claim 17, wherein the outer surface of said inferior endplate is generally convex between the anterior sidewall and the posterior sidewall.

19. The expandable interbody fusion device of claim 16, wherein in the expanded condition said anterior edge is higher than said posterior edge.

* * * * *